US010070790B2

(12) United States Patent
Fitzgerald et al.

(10) Patent No.: US 10,070,790 B2
(45) Date of Patent: Sep. 11, 2018

(54) NEUROMECHANICAL ALGOMETER

(71) Applicant: Rehabilitation Institute of Chicago, Chicago, IL (US)

(72) Inventors: Colleen M. Fitzgerald, LaGrange, IL (US); Yasin Y. Dhaher, Mount Prospect, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 92 days.

(21) Appl. No.: 14/213,880

(22) Filed: Mar. 14, 2014

(65) Prior Publication Data
US 2014/0275846 A1    Sep. 18, 2014

Related U.S. Application Data

(60) Provisional application No. 61/799,553, filed on Mar. 15, 2013.

(51) Int. Cl.
*A61B 19/00*    (2006.01)
*A61B 5/00*    (2006.01)
*A61B 5/0492*    (2006.01)

(52) U.S. Cl.
CPC .......... *A61B 5/0053* (2013.01); *A61B 5/0492* (2013.01); *A61B 5/483* (2013.01); *A61B 5/4827* (2013.01); *A61B 5/6843* (2013.01); *A61B 5/6885* (2013.01); *A61B 2560/0425* (2013.01); *A61B 2560/0462* (2013.01); *A61B 2560/0468* (2013.01); *A61B 2562/0209* (2013.01); *A61B 2562/0247* (2013.01)

(58) Field of Classification Search
CPC .... A61B 5/4824; A61B 5/4827; A61B 5/0053
USPC ........................................................ 600/557
See application file for complete search history.

(56) References Cited

U.S. PATENT DOCUMENTS

| | | | |
|---|---|---|---|
| 4,768,521 A | 9/1988 | Schiffman et al. | |
| 4,928,707 A | 5/1990 | Schiffman et al. | |
| 6,113,552 A * | 9/2000 | Shimazu | A61B 5/4824 600/557 |
| 6,132,387 A * | 10/2000 | Gozani | A61B 5/0488 600/554 |
| 6,185,451 B1 | 2/2001 | Richardson et al. | |
| 6,752,770 B2 | 6/2004 | Mayrose et al. | |
| 2004/0054392 A1 | 3/2004 | Dijkman | |

(Continued)

OTHER PUBLICATIONS

Baguley SD et al. Vaginal algometer: development and application of a device to monitor vaginal wall pressure pain threshold. Physiol. Meas. Nov. 2003; 24(4):833-6.
Tu FF et al. Comparative Measurement of Pelvic Floor Pain Sensitivity in Chronic Pelvic Pain. Obstet. Gynecol. Dec. 2007; 110(6):1244-8.
Tu FF et al. Vaginal Pressure-Pain Thresholds: Initial Validation and Reliability Assessment in Healthy Women. Clin. J. Pain Jan. 2008;24(1):45-50.

(Continued)

*Primary Examiner* — Daniel Cerioni
(74) *Attorney, Agent, or Firm* — Polsinelli PC; Ari M. Bai

(57) ABSTRACT

Systems and methods for the diagnosis of chronic pain are disclosed. An algometer comprising a pressure sensor and electrode is disclosed. The algometer may be used to measure pressure applied by a clinician at a location on a patient's body, along with EMG signals emanating from the same location of the patient. Further, a pain trigger operable by the patient may be used in coordination with the algometer. Data from the algometer and pain trigger are transmitted to a computing device and display for rendering and analysis of patient data, leading to improved diagnosis.

14 Claims, 11 Drawing Sheets

(56) References Cited

U.S. PATENT DOCUMENTS

| | | | | |
|---|---|---|---|---|
| 2005/0192567 A1* | 9/2005 | Katims | ............... | A61B 5/0484 |
| | | | | 606/41 |
| 2008/0097236 A1* | 4/2008 | Kuban | ................ | A61B 5/0053 |
| | | | | 600/557 |
| 2009/0082830 A1* | 3/2009 | Folkerts | ............ | A61B 5/04882 |
| | | | | 607/48 |
| 2009/0088661 A1* | 4/2009 | Suzuki | .................. | G01G 19/50 |
| | | | | 600/547 |
| 2009/0270963 A1 | 10/2009 | Pelger et al. | | |
| 2010/0036280 A1* | 2/2010 | Ballegaard | ........... | A61B 5/4035 |
| | | | | 600/552 |
| 2012/0046580 A1* | 2/2012 | O'Brien | ............... | A61B 5/4029 |
| | | | | 601/47 |

OTHER PUBLICATIONS

Tu FF et al. Pelvic floor pressure-pain thresholds: A pilot study. J. Pain 2006, 7(4), S30.

Bottin A et al. Development of EMG and Pressure Probes for Pelvic Floor Analysis. Available at http://www.lisin.polito.it/english/annual_reports/ar2002_uk/56uk.htm.

Bernhardt O et al. Reliability and validity of a new fingertip-shaped pressure algometer for assessing pressure pain thresholds in the temporomandibular joint and masticatory muscles. J. Orofac. Pain 2007 Winter 21(1), 29-38.

InCare(R) Sensor for Biofeedback and Electrical Stimulation. Feb. 26, 2010. Available at http://www.biomation.com/inco/Pics/incare_sensors_brochure.pdf.

* cited by examiner

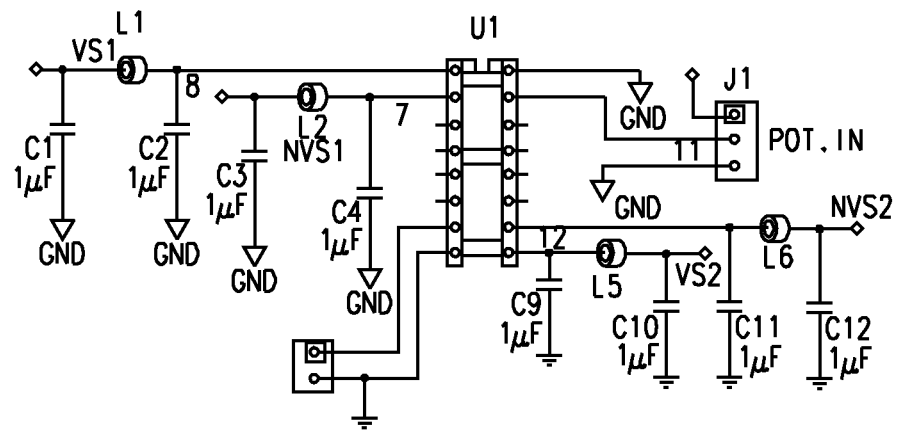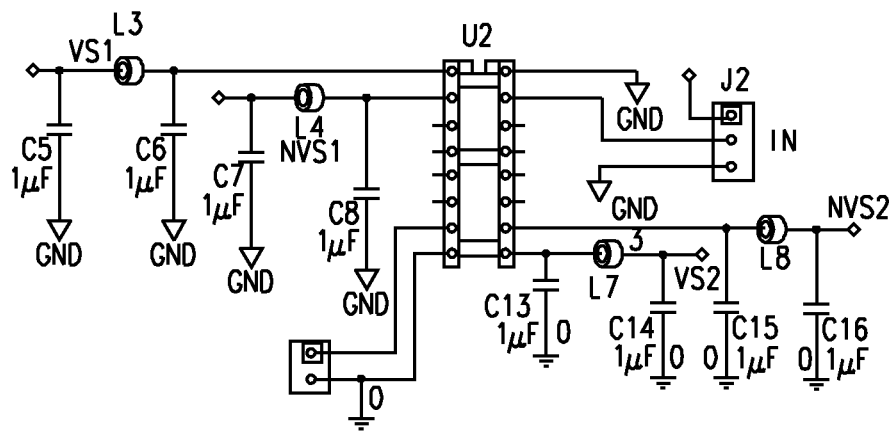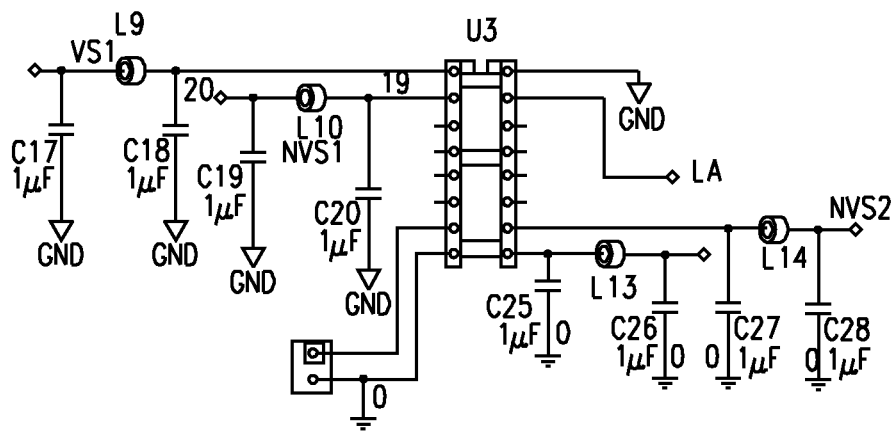
F I G . 7 A

NEUROMECHANICAL ALGOMETER

CROSS-REFERENCE TO RELATED APPLICATIONS

The application claims benefit to U.S. provisional patent application Ser. No. 61/799,553 filed on Mar. 15, 2013 and is herein incorporated by reference in its entirety.

STATEMENT REGARDING FEDERALLY SPONSORED RESEARCH OR DEVELOPMENT

This invention was made with government support under K12 HD055884-01 awarded by the National Institutes of Health. The government has certain rights in this invention.

BACKGROUND

The invention relates to a novel system for the diagnosis and treatment of pain such as pelvic pain.

Chronic pain is a significant and highly prevalent health condition that exceeds the cost burden of heart disease, cancer and diabetes in the United States. Women comprise a majority of all chronic pain populations, particularly persistent pelvic pain. As many as one in three women have some pelvic floor muscle disorder. Female chronic pelvic pain (CPP) is a rapidly growing health concern, consuming as much as $2.8 billion per year in health care services. CPP may reflect a number of underlying pain conditions including endometriosis, interstitial cystitis (IC), vulvodynia and pregnancy-related pelvic pain. CPP affects reproductive age women's physical ability, quality of life, psychological health and sexual function. Certain pelvic conditions, even if they do not cause pain, are responsible for undesirable effects such as incontinence. Men also suffer from CPP, from such underlying pain conditions as chronic prostatitis.

The current mechanistic understanding of CPP in women is not well understood in the prior art. Different types of CPP diagnoses often demonstrate overlapping clinical presentations, and the diagnosis often varies depending on which specialist is evaluating the patient. Given the lack of empirical evidence, treatment of CPP can be haphazard and indiscriminate, with few validated interventions emerging from significant research efforts.

Recent attempts have been made to revise diagnostic and treatment algorithms. For example, the UPOINT (Urinary, Psychosocial, Organ specific, Infection, Neurologic system, Tenderness of Skeletal Muscles) system for clinical phenotyping in women with CPP focuses on localized (organ) versus systemic differentiation. There have also been efforts to evaluate CPP by studying the overlapping comorbidities. However, even with these revised attempts to classify, scientific findings have failed to identify the causative mechanisms to guide treatment.

Treatment of CPP can be haphazard and indiscriminate, with few validated interventions emerging from significant research efforts. Recent attempts have been made to revise diagnostic and treatment algorithms. For example, the UPOINT (Urinary, Psychosocial, Organ specific, Infection, Neurologic systemic, Tenderness of Skeletal Muscles) system for clinical phenotyping in women with CPP focuses on localized (organ) versus systemic differentiation. There have also been efforts to evaluate CPP by studying the overlapping comorbidities. However, even with these revised attempts to classify, scientific findings have failed to identify the causative mechanisms to guide treatment.

Understanding the etiology responsible for CPP requires a dissection of peripheral and central pain mechanisms. Normal female pelvic physiology consists of somatic and visceral components that act alone and in tandem. Peripheral factors include sensory somatic ($A\beta/A\delta$ mechanical nociceptors, unmyelinated C fibers), muscular, visceral and viscero-somatic crosstalk. IC patients have demonstrated bladder hyperalgesia and have altered response to thermal stimuli. Muscle tenderness has been reported in pregnancy-related pelvic pain. Animal models of pelvic pain have reinforced the role of increased sensory hyperinnervation, visceral afferent sensitization, and muscular tension, including parturition pain. Such peripheral changes are known to culminate in spinal cord (central) sensitization as pain transitions to chronicity. Alterations in brain function and structure in male and female pelvic pain have been shown. A comprehensive mechanistic understanding of female pelvic pain requires concurrent peripheral and central measures.

While a comprehensive mechanistic understanding of CPP does not exist, certain CPP subtypes are predominated by prototypical somatic features. Pregnancy-related CPP, for example, appears to be a purely somatic musculoskeletal subtype. It is localized, intermittent, and typically provoked by movement. The pathogenesis of this subtype is not known, but has focused on musculoskeletal etiologies with no effort made to study the sensory/peripheral neural or central influences. Other CPP subtypes are predominated by visceral features. IC, for example, represents a visceral CPP subtype dominated by a diffuse, constant, and often unprovoked pain presentation. Few studies have identified sensory or and muscular abnormalities in IC, and functional brain correlates to bladder distension have only been examined in healthy controls. Somatic and visceral components may act alone or in tandem.

Previous work in mechanical pressure sensitivity to $A\beta/A\delta$ mechanoreceptors indicates that mean pressure pain detection thresholds at multiple vaginal sites are significantly lower in women with CPP (not pregnancy related) compared with healthy controls. The pelvic joints (sacroiliac joint and pubic symphysis) are thought to be the most common regional sources of postpartum CPP. Several clinical physical examination tests have been found to be sensitive and specific for pregnancy-related CPP especially when used in combination. Unfortunately, these examination maneuvers do not differentiate the exact peripheral nociceptors nor do they include vaginal pelvic floor muscle (PFM) assessment. Data indicates an association with sacroiliac pelvic pain and PFM tenderness. In a biomechanical model, the PFM appears to reduce the shear of the sacroiliac joint in a standing posture. In theory, this protective effect may be influenced by PFM injury during vaginal delivery. Preliminary data shows that most postpartum women with pelvic pain have PFM tenderness on vaginal examination compared to women without pain (FET). Indirect assessment of PFM kinematics has been conducted by abdominal ultrasound for somatic-musculoskeletal pelvic pain.

Pressure therapy is known in the art as a means of reducing pain in patients with pelvic pain. A pressure algometer may be used to measure a patient's sensitivity to pressure or to pain. Information obtained from such measurements is used in the art to identify an appropriate course of therapy for patients. For instance, applying pressure greater than a pre-determined threshold may result in pain improvement in patients. It is also known in the art that pelvic muscles, like other muscles in the body, generate varying amounts of electrical potential. Electromyography techniques with electrodes are used to evaluate and record the electrical activity produced by muscles (e.g. EMG signals).

Quantitative sensory testing (QST) is a standard approach to experimentally testing peripheral sensory abnormalities across diverse chronic pain populations. QST protocols have become standard measures in chronic pain states and alone they have failed to provide sufficient information about distinct pain mechanisms. However, CPP subtypes have received minimal to no attention (postpartum) in this respect, and existing studies have typically focused on few sensory modalities, rather than conducting comprehensive assessments of CPP sensory alterations. Peripheral nociceptors that relay pelvic pain signals include neuromuscular (i.e., $A\beta$ and $A\delta$ mechanoreceptors, unmyelinated C fibers) and visceral afferents, which can be segregated into pinprick, mechanical, thermal, and distension sensory modalities.

Considering the scope and importance of medical study on pelvic conditions and pelvic pain, relatively little research has focused on the development of objective measurements of optimal pressure to be applied to a pelvic area. Similarly, little research has been performed to determine baseline EMG signals of pelvic muscles, either in healthy patients or in patients with pelvic conditions.

BRIEF SUMMARY

There is a substantial need by physicians in obstetrics and gynecology, as well as other medical providers, such as physical therapists, (herein, "clinicians") for a diagnostic system and methods that can be used to accurately and simultaneously measure the amount of pressure applied to a pelvic region, the EMG signals emanating from that region, and the patient's pain sensitivity in response to the applied pressure. One embodiment of the invention consists of a system that utilizes applied pressure, EMG monitoring, and pain assessment for the assessment of CPP. The system may include a novel algometer, which includes a pressure sensor and an electrode for the sensing of EMG signals from a patient's body. The system may further include a patient-activated pain trigger device. The system may further include processing and analyzing computing modules that receive signals from the pressure sensor, the electrode, and the pain trigger, and present a representation of the information from these devices upon a graphical display. The invention allows clinicians to provide more timely and targeted interventions to improve the quality of life of women with CPP and other patients.

BRIEF DESCRIPTION OF THE DRAWINGS

FIGS. 7A-7C are a schematic of EMG insulation used in one embodiment of the invention.

DETAILED DESCRIPTION

Figure 5:
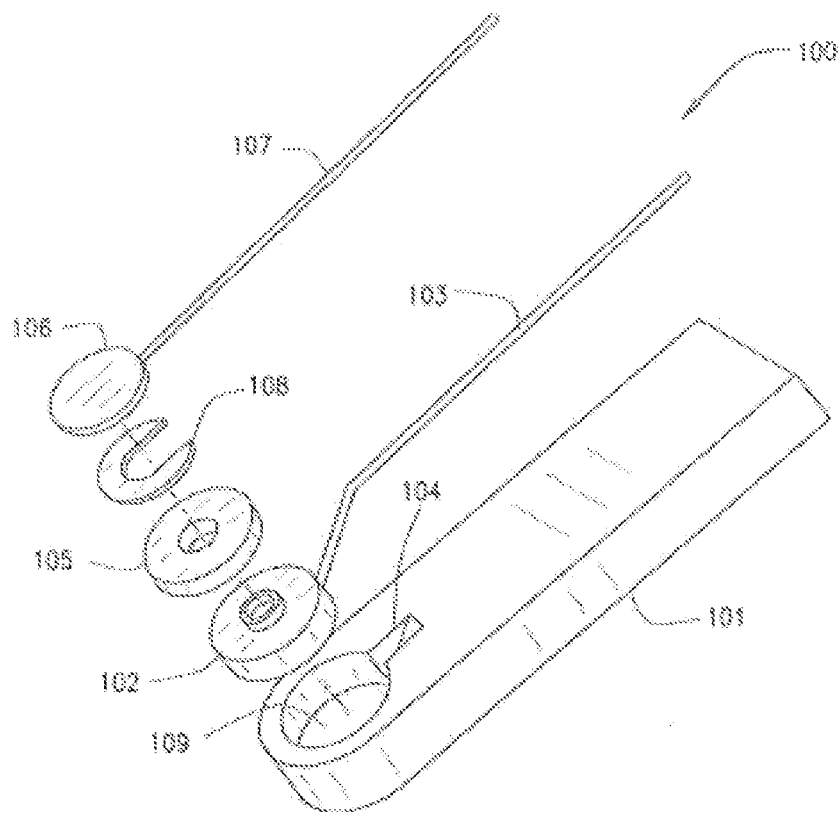
FIG. 5 is an exploded view of an embodiment of the algometer.

Algometer. In one embodiment shown in FIG. 5, the housing 101 of the algometer, designated 100, defines an opening 112 along a proximal end of the housing 101 and is shaped such that it may be worn over the finger of a clinician. The housing 101 may be made of plastic or other material that is suitable to be worn by a clinician for insertion in a patient's vagina, anus, or other orifice. At the tip of the housing 101, under the space for the distal phalange of the clinician's finger, an opening 109 exists that allows for insertion of a pressure sensor 102. The pressure sensor 102 may be one known in the art, such as a uniaxial load sensor. The pressure sensor 102 may be sized and shaped such that it fits snugly within the opening 109 of the housing 101. In some embodiments, pressure sensor 102 may be circular, with a diameter such that it fits comfortably underneath fingertip of the clinician. Pressure sensors 102 of other sizes and shapes may also be used, such that they avoid unnecessary discomfort to the patient. This design allows for the instantaneous measurement of the pressure level a clinician applies to a specific area of a patient and the associated neuromuscular response.

Figure 6:
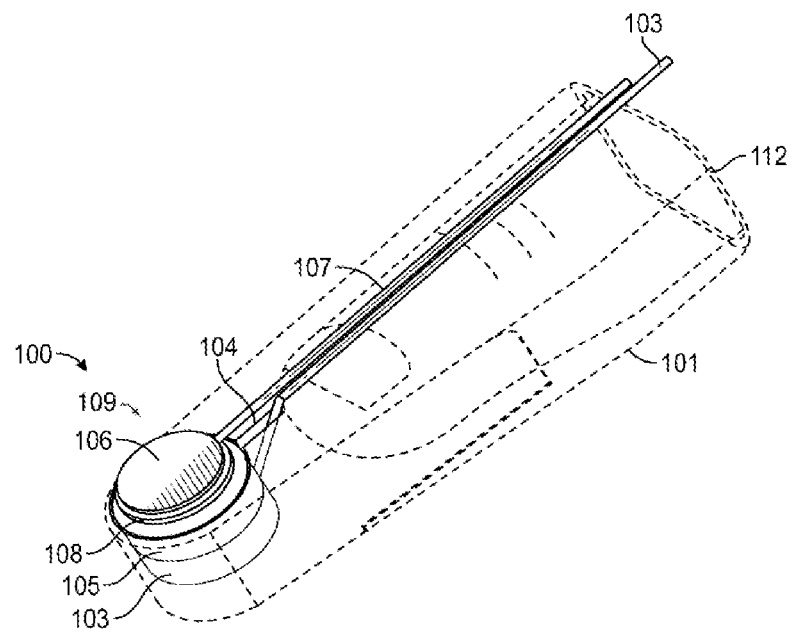
FIG. 6 is an assembled perspective view of the embodiment of the algometer of FIG. 5.

A magnet 105 may also be included within the opening 109 in the housing 101. In one embodiment, the magnet 105 is sized to fit within the opening 109 of the housing 101 and over the pressure sensor 102. An electrode 106 may then be coupled to the algometer 100 by a magnetic force. The opening 109 of the housing 101 may further be sized such that the electrode 106 is flush with the bottom of the opening 109, and does not extend beyond the opening 109. This arrangement avoids an "edge effect" that could otherwise cause pain to a subject due to the edge of the electrode 106 running against sensitive skin during clinical use. The pressure sensor 102 (also known as a force sensor) is further secured into the housing 101 by fitting the magnet 105 over the pressure sensor 102. As shown, housing 101 fits over the finger of a clinician, i.e., the opening 112 defined by the housing 101 receives the finger. Pressure sensor 102 fits into the opening 109 of the housing 101. Wire 103 connects the pressure sensor 102 to the data acquisition module (described below) and is configured to fit into groove 104 of the housing 101. Magnet 105 also fits into the opening 109 of housing 101 and over the pressure sensor 102. A protective glove (not shown) may be worn by the clinician, after inserting her examining finger into the opening 112 defined by the housing 101 of the algometer 100, so that the glove physically separates magnet 105 and electrode 106. Electrode 106 is connected to a data acquisition module 350 via wire 107. A washer 108 may be coupled to electrode 106 to assist with alignment, but is not necessary. FIG. 6 represents an assembled view of one embodiment of the algometer 100.

One advantage of assembling the algometer 100 as described above is that it allows the clinician to wear a latex or other protective glove over the algometer 100, to prevent the algometer 100 from being infected during clinical use. In this embodiment, the pressure sensor 102 and magnet 105 are inserted into the housing. The clinician then inserts her finger into the opening 112 defined by the algometer housing 101 and puts on a latex or other protective glove. The clinician then places the electrode 106 to the part of the glove over the magnet 105, which results in the electrode 106 being coupled to the algometer 100 by magnetic force. When used in this fashion, the only component of the algometer 100 that makes contact with the patient's skin is the electrode 106. This technique reduces the number of components that require sterilization after each use. Specifically, the only element of the algometer 100 that requires sterilization after use is the electrode 106. Alternately, the algometer 100 may be assembled and used such that each part may be individually sterilized after use, or that the algometer 100 is disposed after use. Another advantage is that the pressure sensor 102 and the electrode 106 are applied over the same area of the patient's skin, allowing for the recording of pressure and EMG information at the same spot on the patient. Commercially available surface electrode systems, such as those offered by Delsys (Boston, Mass.) may be used.

The pressure sensor 102 instantaneously measures the amount of pressure a clinician applies to a patient. The pressure sensor 102 is coupled either by wire or wirelessly to a data acquisition module 350. When a wire is used, the housing 101 is designed such that the wire may run from the pressure sensor 102 without interfering with the clinician's use of a latex or other protective glove. Where wireless technology is used, such as Bluetooth, the housing 101 of the algometer 100 allows space for insertion of the necessary power and data components as well as the wireless transmitter or transceiver for communication to the receiver or transceiver coupled to the data acquisition module 350. In one embodiment, the maximal pressure measured by the pressure sensor 102 is approximately 5 kg/cm$^2$.

Figure 8A:
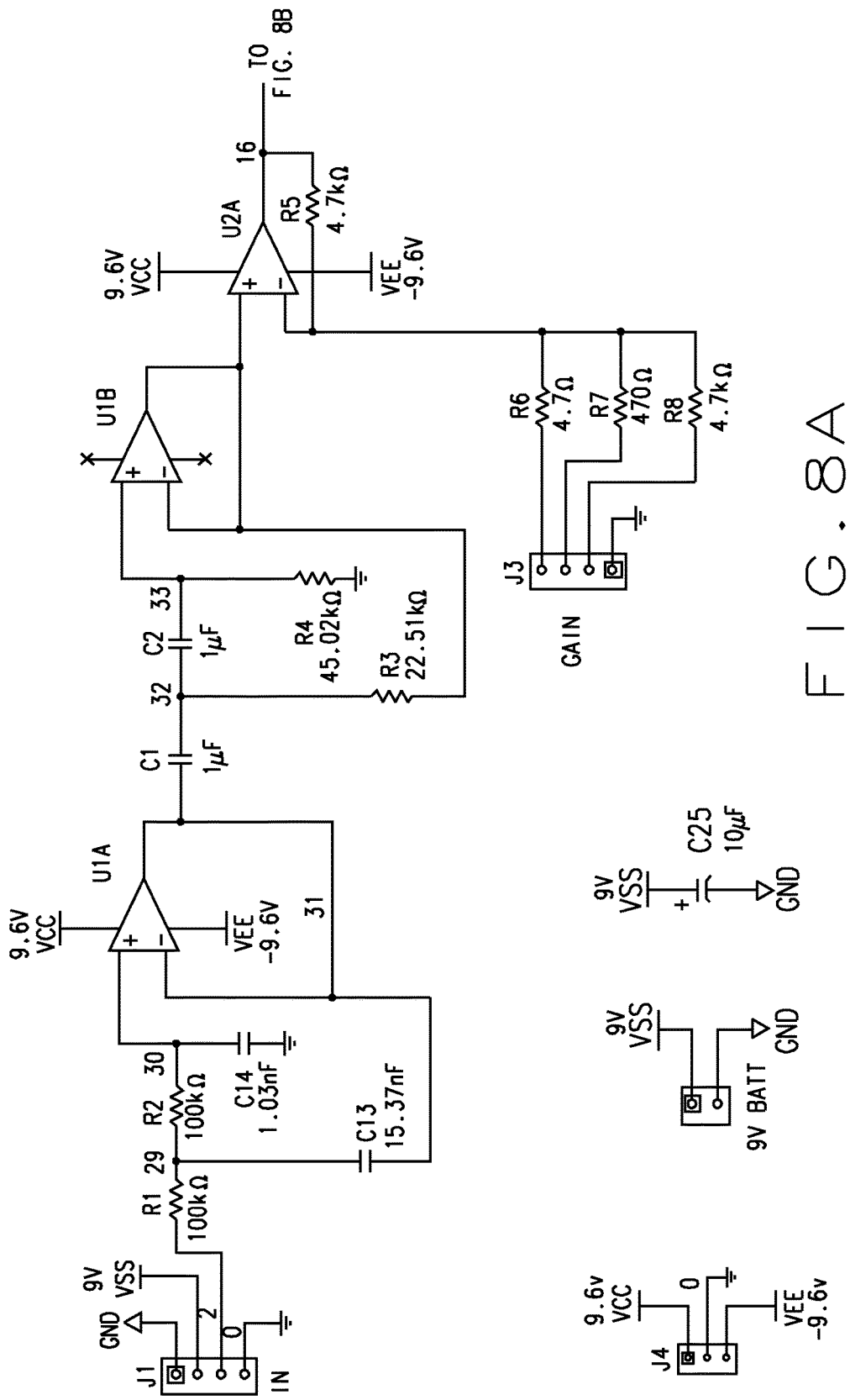
FIGS. 8A and 8B are a schematic of an EMG low pass/high pass/notch amplifier used in one embodiment of the invention.
Figure 8B:
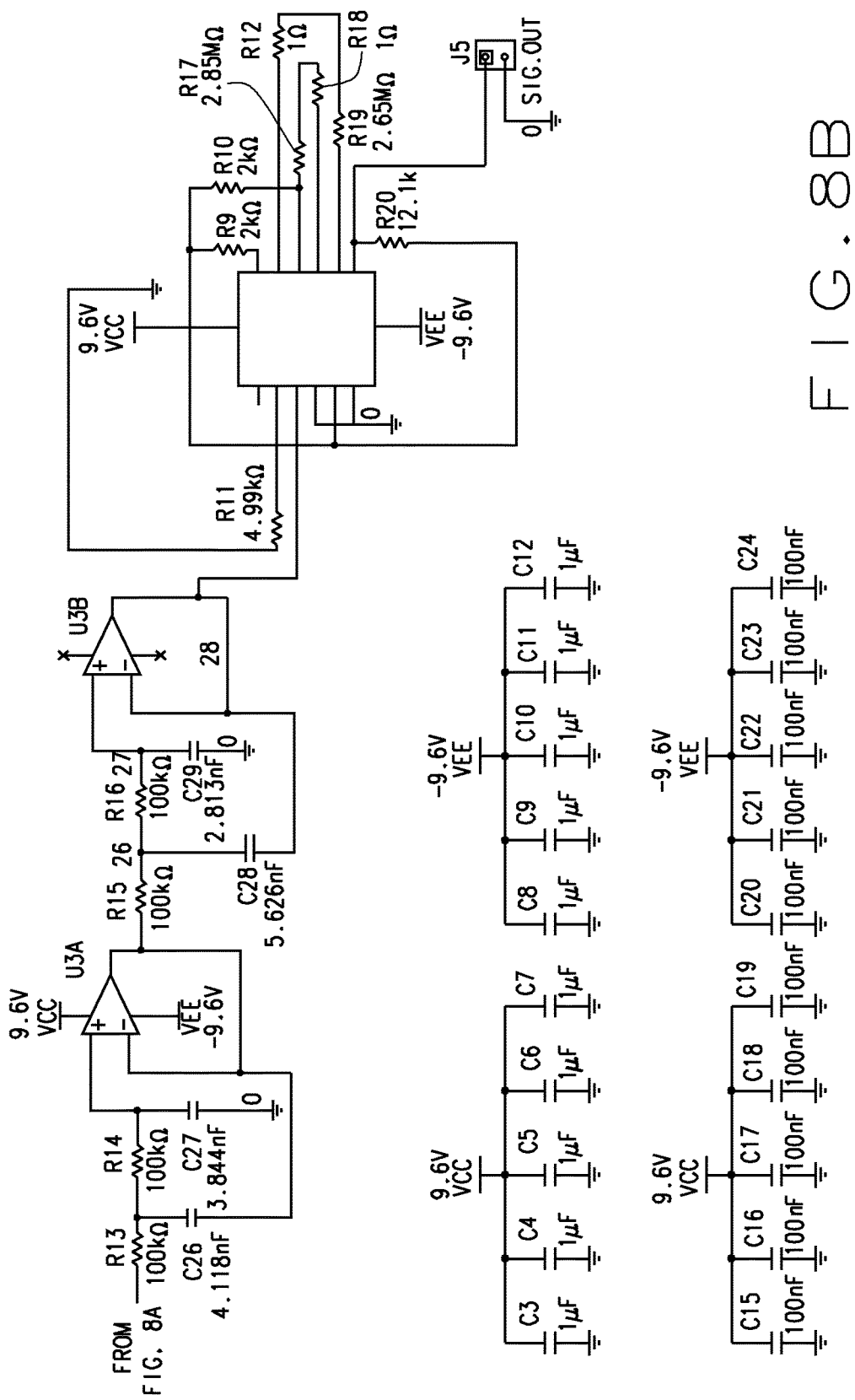

The electrode 106 simultaneously records muscle activation at the same anatomic site as the pressure measurement. In one embodiment, the system includes an electrode isolation circuit 302 to prevent across-electrode grounding that would potentially be mediated by body fluids. Double electrodes with a single ground may be used to determine the EMG signals. Alternatively, such a system may not sufficiently reduce noise between the electrodes applied to the patient's skin and the ground. Or, such a system may produce irrelevant data, for instance in a moist environment when the electrodes are shunted. In another embodiment, the algometer 100 utilizes an electrode 106 with a double ground to more accurately measure EMG signals. In one such embodiment, the electrode 106 is connected by wire 107 to the data acquisition module 350. The data acquisition module 350 is connected by yellow wire 360 to ground A 365 and by black wire 370 to ground B 375, as shown in FIG. 12. During clinical use, each ground 365 and 375 is attached to a separate bony landmark of the patient, such as the left and right knee or the left and right pelvic bone crest. After determining the potential $V_1$ between the electrode 106 and ground A 365 and the potential $V_2$ between the electrode 106 and ground B 375, the data acquisition module 350 compares $V_1$ and $V_2$. The EMG activity will be calculated as the change of mV from baseline and will be normalized by the maximum voluntary contraction (MVC) of the patient. EMG activity is then relayed to the data acquisition module 350. The data acquisition module 350 includes a filter 353 to filter remaining environmental noise. For instance, a notch filter, such as the filter disclosed at FIG. 8, may be used to filter signals at 60 Hz and above, to filter noise from sources such as clinical office lighting and also to filter other grounding issues. Use of the electrode 106 allows the clinician to detect local EMG activity in a small region of the patient's muscle, which may indicate a muscle tear or other condition or impairment. The EMG signal may be transmitted by cable or wireless means to a data acquisition module 350 that is connected (by wires or wireless means) to a personal laptop, tablet, or other computing device 300.

Pain Trigger. The pain trigger 200 is activated by the patient when the amount of applied pressure has become painful. The pain trigger 200 is used by the patient, and it sends data representative of the patient's squeezing of the trigger to the computing device 300 for further analysis and display. Data from the pain trigger 200 may be transmitted to the data acquisition module 350, for instance if the data acquisition module 350 is external to the housing 101. Alternately, data from the pain trigger (not shown) may be transmitted directly to the computing device 300. In one embodiment, the pain trigger consists of an adjustable handle that opens and closes via a pivot. The patient may open or close the handle to indicate the amount of pain caused by application of pressure by the clinician, with closed indicating no pain, full open indicating full pain, and intermediate openings indicating intermediate amounts of pain. Alternatively the pain trigger could be a squeeze device, which transmits a binary value simply indicating whether or not the patient experiences pain, whereby the patient squeezes the device to indicate she is in pain. When in use, the pain trigger sends continuous signals reflecting its state, and therefore reflecting in real time whether the patient is experiencing pain and in certain embodiments, how much normalized pain the patient is experiencing.

Figure 9:
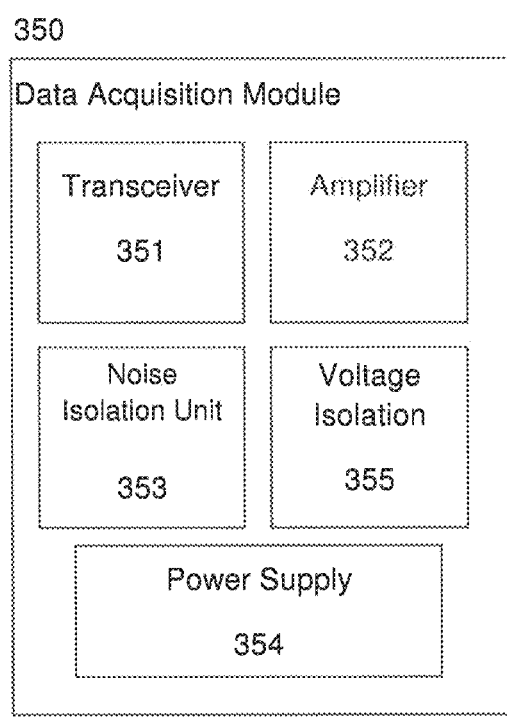
FIG. 9 is a simplified block diagram of data acquisition module.
Figure 10:
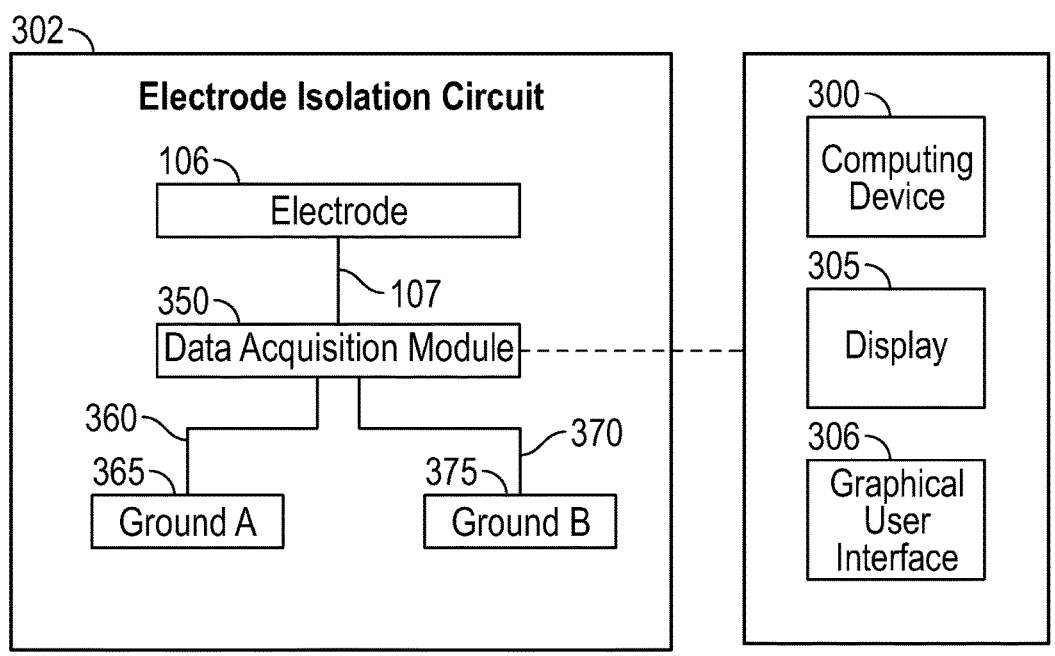
FIG. 10 is a simplified block diagram of electrode isolation circuit in communication with a computing device and a display.

Data acquisition module. Signals from the pressure sensor 102 and electrode 106 are transmitted to the data acquisition module 350. In one embodiment, the data acquisition module 350 includes a receiver or transceiver 351, an amplifier 352, a noise isolation unit 353, a power supply 354, and voltage isolation 355, as shown in FIG. 9. The data acquisition module 350 includes a power module, such as a battery, a connection to AC or other power outlet for battery charging, and the necessary isolation components. In one embodiment, the data acquisition module 350 is powered by low-voltage, 12V battery cell that supplies two internal DC/DC +−9V and +−5V convertors. The electrode 106 is powered with a 5V battery in the data acquisition module 350, similar to those found in cell phones. In one embodiment, the EMG is sampled at 1000 Hz and is low-pass filtered at 500 Hz in the data acquisition module 350. After an offline 10 Hz low pass filtering and full wave rectification, a baseline EMG signal and the corresponding standard deviation is calculated 100 ms prior to the onset of the contraction of a muscle. A window of 120 ms after the onset of the contraction will be used to characterize the level of contraction, indicating how high the contraction is. In another embodiment, the data acquisition module 350 is miniaturized, so that it fits within the housing 101 of the algometer 100. In this embodiment, data from the pressure sensor 102 and the electrode 106 are transmitted via wire or via wireless means, such as Bluetooth, through the data acquisition module 350 inside the housing 101 to the computing device 300. The miniature nature of the data acquisition circuitry results in smaller power requirements. In one embodiment, the housing 101 of the algometer 100 is adapted to be coupled to a charging pad 400 (not shown), similar in size and shape to that of a charging pad for a cell phone. Using the algometer 100 with a miniaturized data acquisition module 350 contained in its housing 101, in combination with a computing device 300 such as a tablet (such as an IPAD® from Apple, Inc., Cupertino, Calif.) with its corresponding display 305, presents clinical efficiencies and increased simplicity of operation.

Figure 7B:
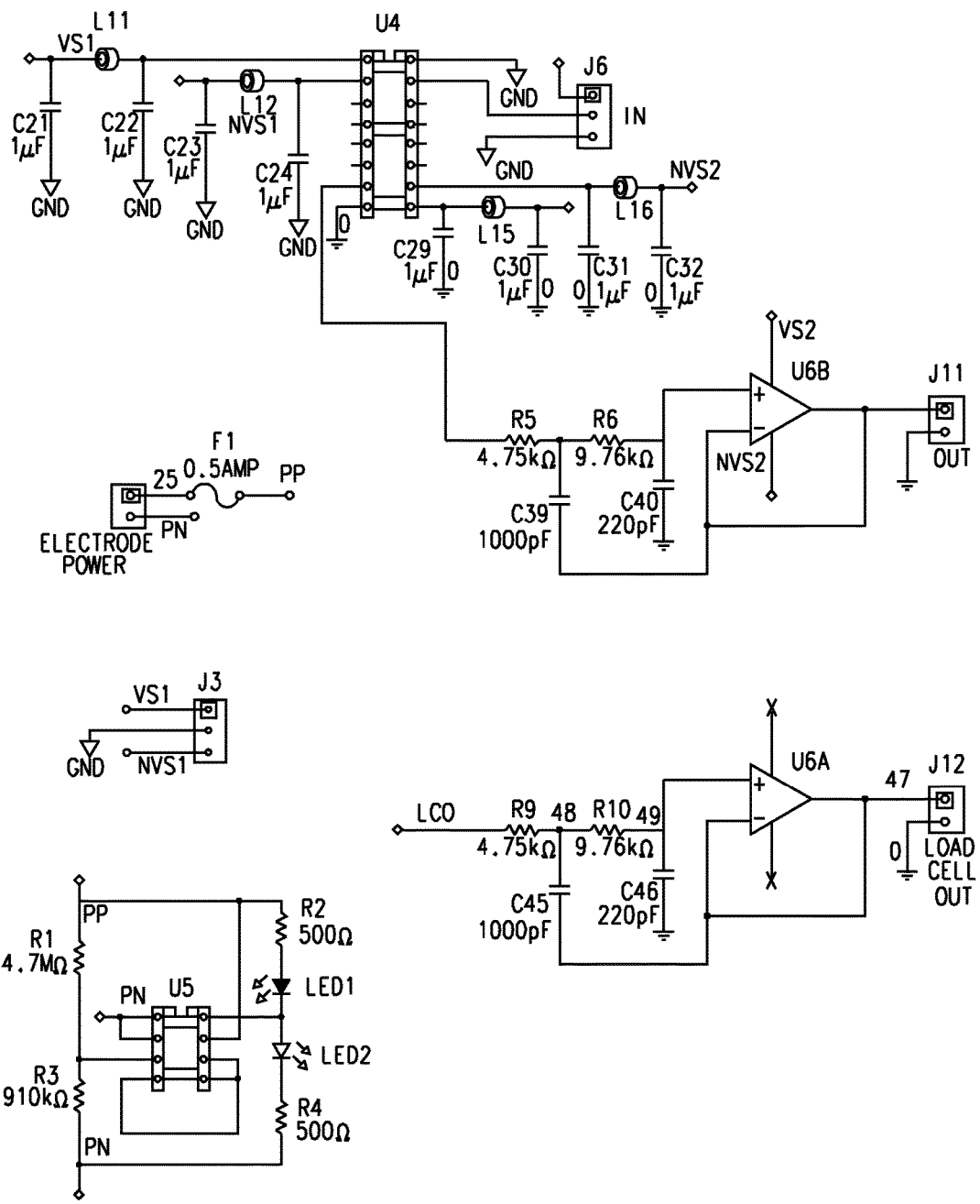
Figure 7C:
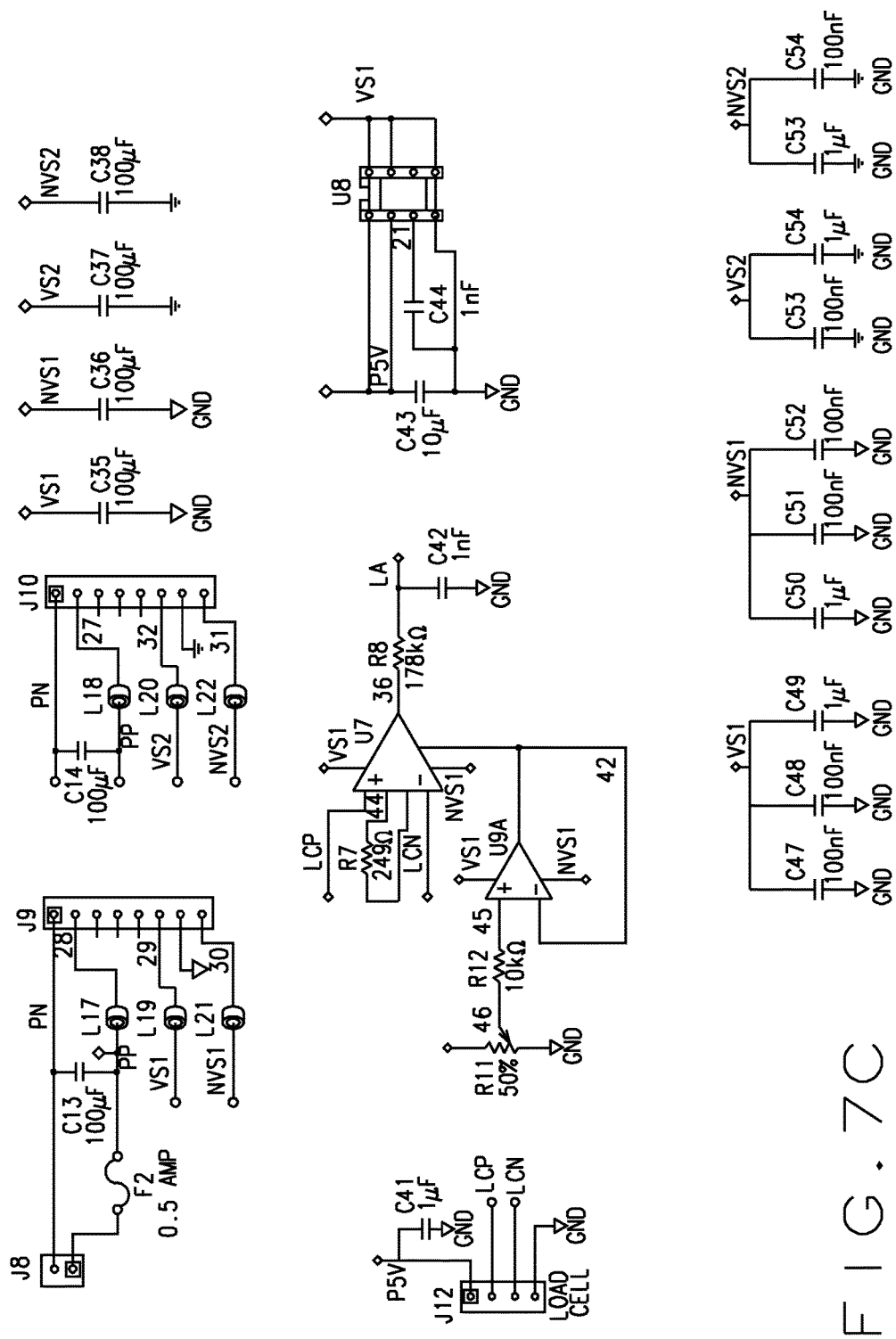

All signals from the electrode 106 and the pressure sensor 102 are insulated, via the circuit disclosed at FIG. 7, and digitally transmitted across a differential capacitive barrier in the data acquisition module 350. This technique guaranties up 1500 Vrms subject protection from the PC-based data acquisition. Additionally, the data acquisition module 350 may be disabled when it is connected to AC outlet for battery charging. The data acquisition module 350 may be part of the computing device 300 (described below), the display 305, or the algometer 100. Alternately, it may be a self-contained device.

Computing device. The computing device 300 receives signals from the pressure sensor 102 and electrode 106 on the algometer 100 and from the pain trigge, either directly or via a data acquisition module 350. Output from the data acquisition module 350 is transmitted via USB or other well known means, including wireless means, to a computing device 300, such as a computer, laptop, personal digital assistant, or smartphone. In one embodiment, the computing device 300 is programmed via Matlab, LabView, or other software to allow for review and analysis of data, which is rendered on a visual display 305 coupled to the computing device 300, for review by the clinician and/or patient. Descriptive statistics (including mean and standard deviation) may be calculated for each sensory and functional test and for EMG MVC for each patient. The display 305 may be connected to the computing device 300, or it may be separate from the computing device 300 but connected, again via wired or wireless methods.

The computer system 302, comprising computing device 300 and display 305, records the signals for further data analysis and displays a visual representation of the information provided by the signals. A computer program tailored to process these data will analyze and interface these measurements using MATLAB (provided by Mathworks of Portola Valley, Calif.) or a similar software package. In one embodiment, when in use, the display 305 continuously displays the amount of applied pressure recorded from the pressure sensor 102 and period during which a participant indicates pain threshold and supra-threshold through the pain trigger, therefore displaying pain intensity across time.

The display 305 is in communication with a graphical user interface 306. As described above, the computing device 300 may be programmed such that data from the outputs of the pain trigger, the pressure sensor 102 and electrode 106 are displayed in real time to the clinician. In one embodiment, the computing device is programmed so that the display 305 marks the time a participant indicates when they first felt the pain (by adjusting the pain trigger to indicate pain intensity across time). The GUI 306 may include a photo or other visual representation of the anatomy being examined by the physician. The clinician may touch a point on the display 305 (which in one embodiment is a touch screen well known in the art) to indicate where on the patient the clinician is applying the algometer 100, allowing the system to correlate data recorded from the algometer 100 and the pain trigger with the physical location of examination. The GUI program 306 may include one or more easy to use pull down menus for post processing and data analysis. A number of output file formats may be incorporated to maximize compatibility with other data visualization and analysis programs. The algometer 100, electrode 106, data acquisition module 350, pain trigger, computing device 300, and display 305 may fit in a portable package, to allow for easy transportation and storage by the clinician. Alternately, the portable package may exclude the computing device 300 and display 305.

The components of the embodiments described herein may be disinfected using Cavicide or another known disinfectant. At the beginning of each test, disinfectant is applied to the algometer 100 and EMG electrode components, the housing 101 of the algometer 100, and the pain trigger. The examiner wears the exam glove over the housing 101, after inserting the pressure sensor 102 and the magnet 105 into the opening 109 of the housing 101. The examiner will use a gloved hand to perform testing, while using her other hand to work the computing device 300. In one embodiment, the system may be activated using the computing device 300, causing the system to start, pause, or stop the recordation of signals from the pressure sensor 102, electrode 106, and/or the pain trigger. Activation may be through a keyboard, a touchscreen, or via voice commands from the clinician such as "record" or "stop." Alternately, the clinician may provide voice commands to indicate the patient being assessed, the part of the patient's anatomy to which the algometer 100 is being applied, or other actions relating to assessment of the patient. If glove breakage is noticed, testing should be stopped immediately and equipment will be disinfected again and a new glove applied. After completion of the study visit, the electrode 106 and wire 107 are subject to a steam sterilization process.

The algometer system may be used in combination with some of the methods described herein. In one embodiment, a set of 8 intravaginal measures will be performed in the lithotomy position, including the bilateral pubococcygeus, the iliococcygeus, and the obturator internus. One vaginal comparison control site may also be measured where minimal muscle activity is expected, such as at the anterior vagina. All measures may be conducted with the clinician's right index finger inserted 5 cm proximal to the introitus. All pain threshold and supra-threshold measurements will be separated from one another by a 30-second break to prevent temporal summation. The entire complement of tests may be repeated, after a 2-minute break, to derive mean measures of pain threshold and corresponding muscle activation for each site. Baseline volitional control may first be measured prior to pressure placement. Pressure may be increased steadily at an approximate rate, such as 0.1 kg/cm$^2$, per second, following a visual guide displayed by the graphical user interface 306 that records study data. This will be repeated once to derive a mean threshold for each site. Once the pressure exam is completed, the participant may perform voluntary contractions and relaxations of the PFM (measured at all sites) which will be quantified by EMG alone. Alternately, the pressure exam and EMG measurement may take place concurrently, with signals from both the pressure sensor 102 and the electrode 106 being provided in real time. A window of 120 ms after the onset of the contraction may be used to characterize the level of contraction. For each electrode-ground pair, the EMG activity may be calculated as the change of mV from baseline. Additionally, Numeric Rating Scale pain scores (NRS 0-10) may be asked at baseline, pain threshold and suprathreshold, and on completion of the examination.

Embodiments of the invention described herein may be used in combination with psychophysical testing (pressure, thermal and pinprick) of the pelvic region, assisting in the correlation of sensory abnormalities with symptom severity.

To measure the CPP-relevant sensory abnormalities, the following QST battery may be performed at pain-relevant locations, including suprapubic (IC), pelvic floor (overlap postpartum/IC), and sacroiliac (SI) joint (postpartum) and a non-dermatomal control location (volar forearm). Although pain threshold abnormalities may exist in these populations, supra-pain thresholds may be tested because they reflect the dynamic properties of the fluctuating pelvic pain reported by patients. Temporal pain summation reflects aberrant central processing of pain, related to the expansion of neuronal receptive fields in the spinal cord or increased excitability of spinal cord neurons. This process uses repetitive exposures to a train of supra-threshold thermal pain stimuli to assess an individual's cumulative perception of pain. Such exposures may more accurately capture peripherally sensitized afferent activity, which would be expected with chronic pain.

One procedure is described as follows. It is understood by those skilled in the art that results of testing may be subject to distraction, boredom, fatigue, or confusion by patients. Alternate testing that differs from the methods described above but accommodates the patient in order to accomplish the goals of the devices and methods described herein should be apparent to one of ordinary skill. Quantitative sensory testing will take place at visit 1. Patients are asked to indicate where on the skin they localize their pain/tenderness to identify referred pain sites. This area will be tested for pain sensitivity, as well as a nonpainful contralateral control site. The temporal summation procedures will follow the same protocol. First, the patient's area (such as the areas around the vaginal clock) is tested for baseline levels of thermal (48° C.), pinprick, or mechanical pain with a single 5-second stimulation. If the stimulus is judged to be painful, a patient rates zero as no pain and 10 as the greatest imaginable pain, with intermediate pain rated accordingly. Temporal summation will be tested by administering 10 rapid, 5 second repetitions of painful thermal, pinprick, or mechanical stimulation. After each stimulation the participant is asked to rate their pain. A five minute break may separate the testings for each sensory modality to reduce likelihood of nociceptor sensitization.

Thermal pain tests to unmyelinated C fibers may be conducted with a thermal stimulator such as the 3×3 cm Peltier offered by MEDOC TSA-2001, Israel. Periods of stimulation and concurrent participant pain ratings are recorded via custom-programmed software using Labview or other known software. Pinprick sensitivity to Aδ mechanical nociceptors may be employed using a device like the NeuroPen, offered by Owen Mumford, Oxfordshire, UK. The device is used to assess temporal summation of mechanical pinprick-induced pain. As described above, pelvic pain in pregnancy may be associated with deep PFM tenderness.

Physical examination tests may be performed, including Bilateral Patrick's Faber test, the Posterior Pelvic Pain Provocation test, long dorsal ligament (LDL) palpation test, pubic symphysis palpation test, the modified Trendelenburg test, and functional stability testing with the active straight leg raise (ASLR) test. Pain sensitivity will be assessed as the pressure-pain detection threshold (the amount of pressure, in kg/cm2, at which an examinee indicates that the applied pressure has become painful). Pressure may be steadily increased at a rate, such as 0.1 $kg/cm^2/s$, allowing for patient discrimination and response when transitioning between pressure and pain. In one embodiment of the device, maximal measurable pressure is approximately 5 $kg/cm^2$. The electrode 106 simultaneously records muscle activation at the same anatomic site as the pressure measurement. Pain location, duration, intensity, functional impact, and symptoms may be analyzed using the VAS pain scale, McGill Pain Questionnaire, Body Pain Diagram, a pain disability index, Pelvic Girdle Questionnaire, Female Genitourinary Pain Index (FGuPI), the interstitial cystitis symptom index and problem indexes (ICSI, ICPI), or similar measure.

Following the QST procedures, bladder sensitivity to volume distension may be performed using an oral water challenge paradigm. Diminished tolerance to volume is characteristic of IC. Traditional volume thresholds for bladder sensitivity may be quantified using noninvasive, three-dimensional ultrasound, which has been shown to be highly accurate for measuring volumes in unrelated studies. This noninvasive method avoids the discomfort and health risks of catheterization.

Figure 1:
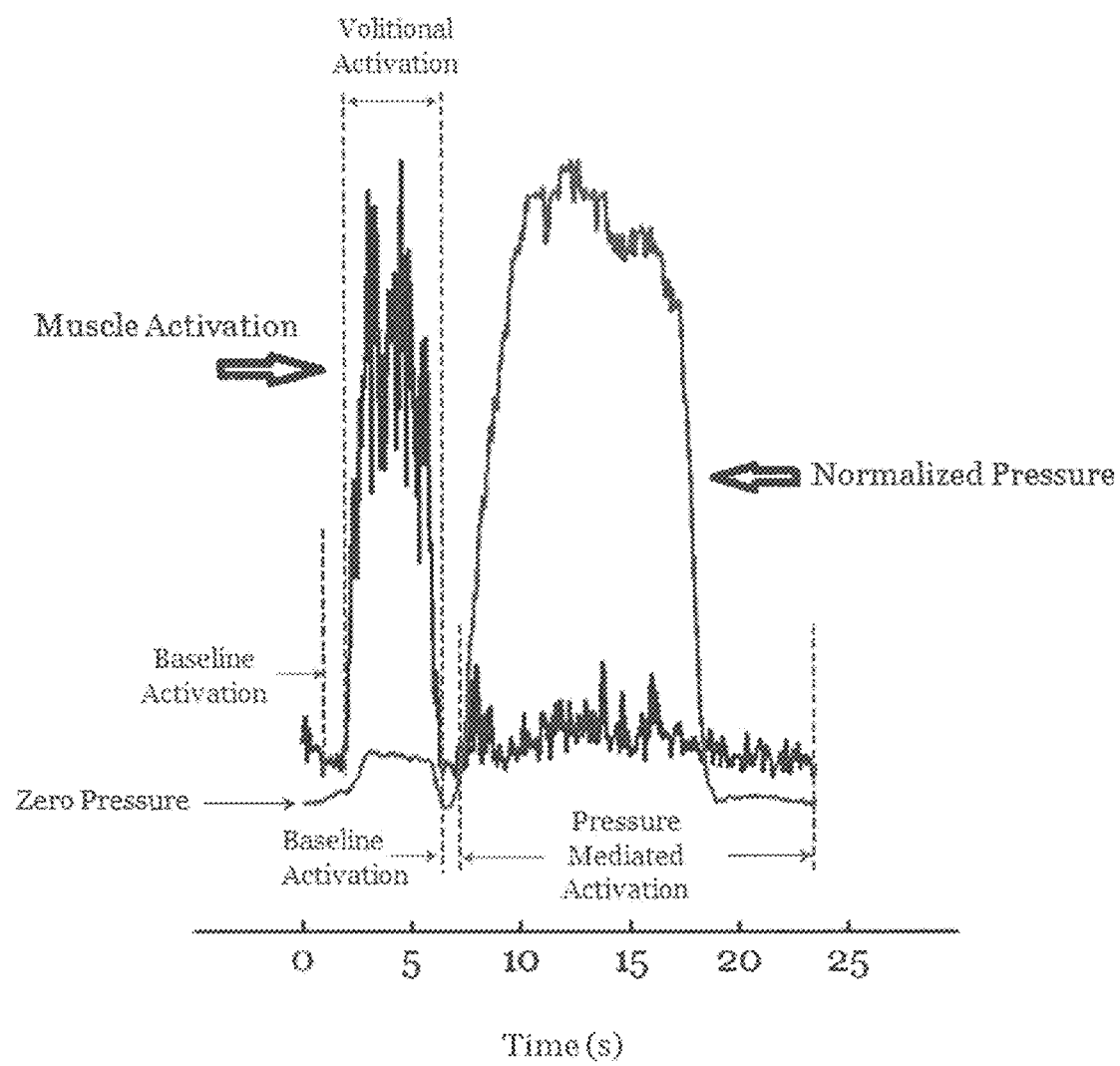
FIG. 1 is a graph showing pressure applied to and EMG signals from a healthy patient using an embodiment of the device disclosed herein.

EMG Testing. Dual ground EMG validation testing was performed against a traditional single ground Delys EMG. The dual ground EMG signal was found to be similar compared to the Delsys EMG signal for muscle activation and resting periods with a more than 99% cross correlation. During additional tests, the locations of the dual grounds showed distinguishable differences in the recorded EMG when the dual grounds were placed at bony locations, such as the knees or pelvic bone crest. As shown in FIG. 1, healthy control subject without pain (n=1) combined pressure sensitivity with simultaneous PFM muscle activation shows evidence of residual pressure with volitional activation (Kegel) and minimal PFM activity with applied pressure. FIG. 1 displays the EMG muscle activation pattern of the right iliococcygeus with pressure induction in a healthy female control without pain. It reveals activation of vaginal wall muscles without cross-talk from other pelvic musculature. Volitional activation (Kegel contraction) is seen following time zero. Initial residual pressure was noted during recording of volitional task. The subject was then cued to relax the vaginal muscles as noted at time 6 seconds. It is likely that the pressure mediated changes observed following the application of the pressure (the pressure curve in FIG. 1) is mediated by the associated muscle stretch reflex.

Figure 2:
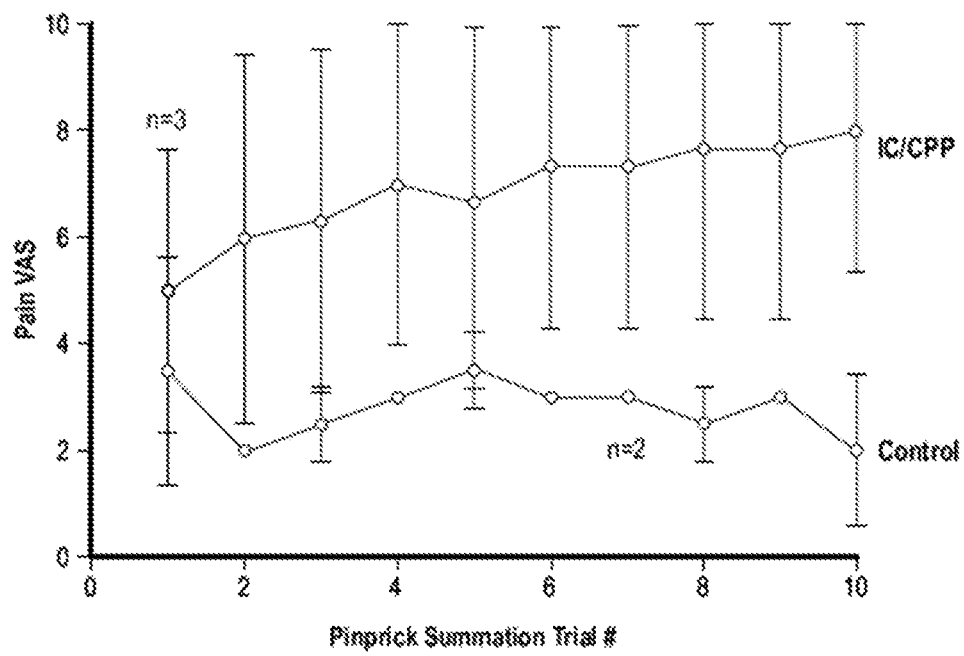
FIG. 2 is a graph showing a comparison of supra-pubic pinprick sensitivity of controls and patients with IC/CPP.
Figure 3:
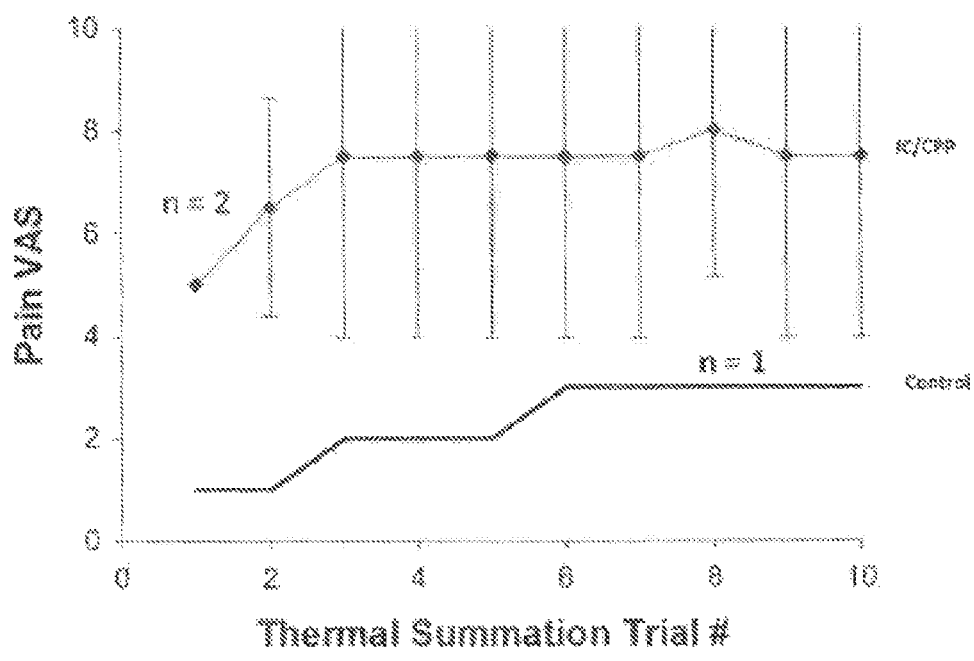
FIG. 3 is a graph showing a comparison of thermal sensitivity of controls and patients with IC/CPP.
Figure 4:
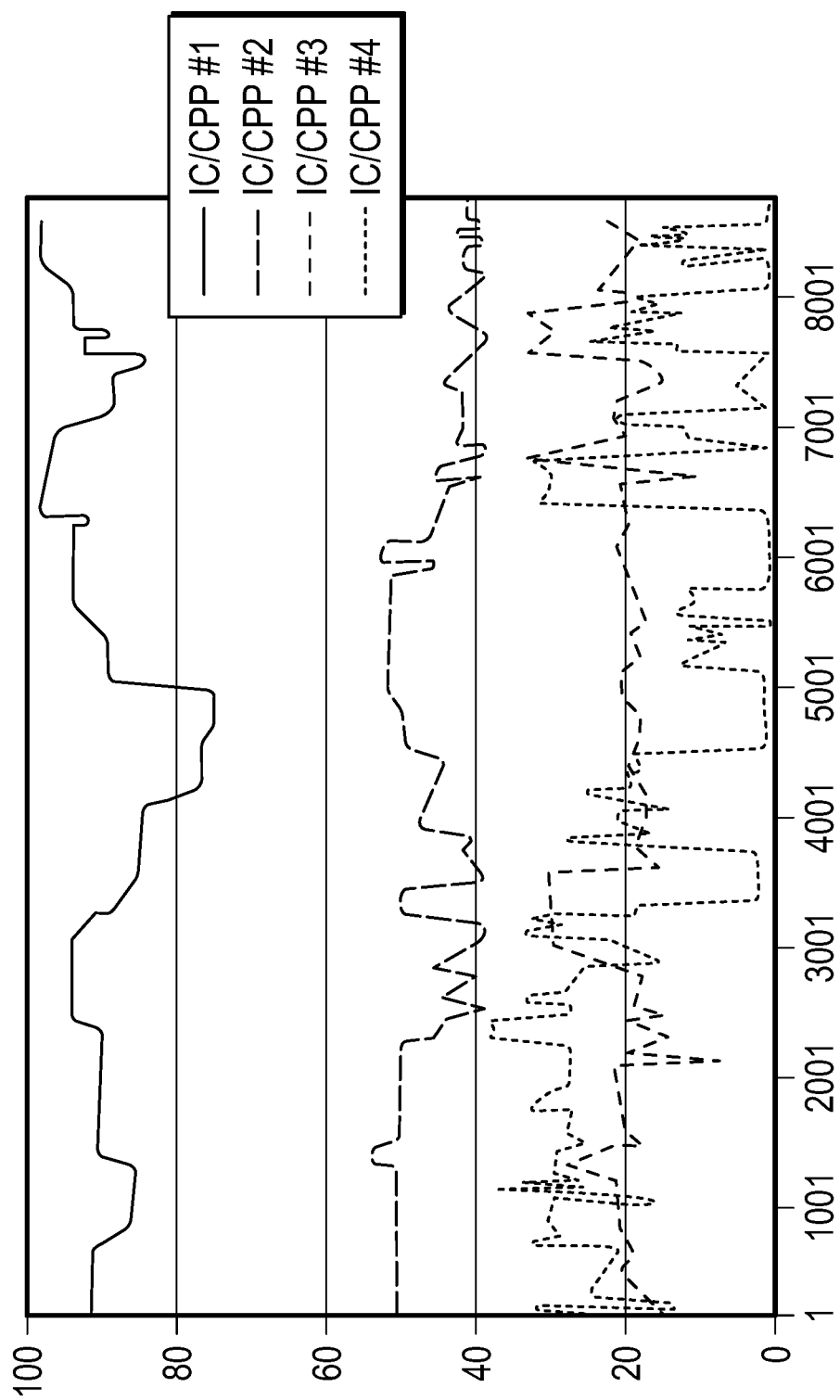
FIG. 4 is a graph showing spontaneous pain vectors from IC/CPP patients.

Preliminary Data in IC/CPP QST. Sensory abnormalities may be seen in IC/CPP compared to matched healthy controls. FIG. 2 discloses women with IC/CPP (n=3) show evidence of elevated supra-pubic pinprick sensitivity, compared to controls (n=2), using a pinprick temporal summation paradigm (10 consecutive pinprick stimuli 5 seconds each, with 2 second inter-stimulus interval). FIG. 3 discloses women with IC/CP P (n=2) show evidence of elevated supra-pubic thermal sensitivity, compared to controls (n=1), using a thermal temporal summation paradigm (10 consecutive thermal stimuli 5 seconds each, with 2 second inter-stimulus interval).

From the preceding description, a number of advantages of one or more aspects, in various embodiments, of the invention are evident. It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. An apparatus for measuring responses from a patient, comprising:
   a housing comprising a proximal end, a distal end, and a bottom surface, the housing defining a first opening at the distal end of the housing and further defining a second opening along the proximal end of the housing shaped to receive a human finger within the housing, the housing configured to receive a human finger into the second opening defined by the housing such that the human finger is oriented towards the distal end of the housing to accommodate the human finger applying an amount of pressure to an anatomic site of the patient;

a pressure sensor oriented within the first opening defined by the housing for measuring the amount of pressure applied to the anatomic site;

a magnet oriented along the first opening of the housing; and an electrode magnetically engaged to the apparatus by the magnet, the electrode configured for measuring one or more electromyographic signals produced by muscle activation of the patient at the anatomic site in response to the applied pressure, wherein the electrode is configured such that when the electrode is magnetically engaged to the apparatus by the magnet, an outer edge of the electrode is flush with an outer edge of the first opening of the housing.

2. The apparatus of claim 1, further comprising a data acquisition module for processing data measured by at least one of the pressure sensor and the electrode.

3. The apparatus of claim 2, wherein the data acquisition module is configured to receive data from at least one of the pressure sensor and the electrode via wireless means.

4. The apparatus of claim 2, wherein the data acquisition module is configured to transmit data to a computing device via wireless means.

5. The apparatus of claim 1, further comprising:
a pain trigger having a state that is configurable by a patient in order to indicate the amount of pain the patient experiences in response to pressure applied to the anatomic site.

6. The apparatus of claim 5, wherein the pain trigger is configured to send continuous signals reflecting the state of the pain trigger.

7. The apparatus of claim 6, further comprising a computing device for receiving and processing data transmitted from the pressure sensor, electrode, and pain trigger.

8. The apparatus of claim 7, further comprising a computer display for displaying the results of data transmitted from the pressure sensor, electrode, and pain trigger processed by the computing device.

9. The apparatus of claim 2, wherein the apparatus further comprises an electrode isolation circuit comprising a double ground for measuring one or more electromyographic signals produced by muscle activation of the patient at the anatomic site.

10. The apparatus of claim 9,
wherein the electrode isolation circuit comprises a first ground wire and a second ground wire,
wherein each of the first ground wire and the second ground wire is configured to be connected to a bony landmark of the patient to generate an electrical potential, and
wherein the apparatus is configured to measure the one or more electromyographic signals produced by muscle activation of the patient at the anatomic site by comparing a first electrical potential between the electrode and the first ground wire with a second electrical potential between the electrode and the second ground wire.

11. The apparatus of claim 1, wherein the pressure sensor is disposed entirely within the housing.

12. The apparatus of claim 1, wherein the housing is shaped for complete insertion into a finger of a protective glove sized to fit a human hand.

13. The apparatus of claim 1, wherein the apparatus is configured so that in a first orientation wherein a protective glove layer is disposed between the housing and the electrode, the electrode is disposed within the first opening such that the bottom surface of the electrode is flush with the bottom surface of the housing and the electrode is so disposed within the first opening by the attraction of a magnetic force.

14. The apparatus of claim 1, wherein the apparatus is configured so that in a first orientation wherein a protective glove layer is disposed between the housing and the electrode, the electrode is disposed within the first opening such that the bottom surface of the electrode is flush with the bottom surface of the housing and the electrode is so disposed within the first opening by the attraction of a magnetic force provided by the magnet.

* * * * *